United States Patent
San et al.

(10) Patent No.: US 9,598,696 B2
(45) Date of Patent: Mar. 21, 2017

(54) BACTERIA AND METHOD FOR SYNTHESIZING FATTY ACIDS

(71) Applicant: William Marsh Rice University, Houston, TX (US)

(72) Inventors: Ka-Yiu San, Houston, TX (US); Mai Li, Houston, TX (US)

(73) Assignee: William Marsh Rice University, Houston, TX (US)

( * ) Notice: Subject to any disclaimer, the term of this patent is extended or adjusted under 35 U.S.C. 154(b) by 228 days.

(21) Appl. No.: 14/350,544

(22) PCT Filed: Oct. 16, 2012

(86) PCT No.: PCT/US2012/060471
§ 371 (c)(1),
(2) Date: Apr. 8, 2014

(87) PCT Pub. No.: WO2013/059218
PCT Pub. Date: Apr. 25, 2013

(65) Prior Publication Data
US 2014/0273114 A1    Sep. 18, 2014

Related U.S. Application Data

(60) Provisional application No. 61/548,005, filed on Oct. 17, 2011, provisional application No. 61/548,399, filed on Oct. 18, 2011.

(51) Int. Cl.
*C12N 1/20* (2006.01)
*C12N 15/00* (2006.01)
(Continued)

(52) U.S. Cl.
CPC .............. *C12N 15/70* (2013.01); *C07K 14/24* (2013.01); *C12N 9/16* (2013.01); *C12N 15/52* (2013.01);
(Continued)

(58) Field of Classification Search
CPC .................................. C12N 9/16; C12P 7/6409
See application file for complete search history.

(56) References Cited

U.S. PATENT DOCUMENTS 7,211,415 B2    5/2007    Rieping
7,553,645 B2    6/2009    Dusch
(Continued)

FOREIGN PATENT DOCUMENTS

EP    12842369    10/2012
WO    2009006430    1/2009
(Continued)

OTHER PUBLICATIONS

Campbell JW, Cronan JE Jr. 2001. *Escherichia coli* FadR positively 20 regulates transcription of the fabB fatty acid biosynthetic gene. J Bacteriol. 183(20):5982-90.
(Continued)

*Primary Examiner* — Yong Pak
(74) *Attorney, Agent, or Firm* — Boulware & Valoir

(57) ABSTRACT

The present invention discloses a process for increasing the production of free fatty acids at high yield (close to maximum theoretical yield), with various fatty acid compositions and various percentage of fatty acids accumulated intracellularly. This invention will enable the efficient production of other products derived from free fatty acids and/or products that can be branched out from the fatty acid synthesis pathways.

18 Claims, 4 Drawing Sheets

(51) Int. Cl.
  *C12N 9/16* (2006.01)
  *C12N 9/00* (2006.01)
  *C12Q 1/68* (2006.01)
  *C12P 7/64* (2006.01)
  *C07H 21/04* (2006.01)
  *C12N 15/70* (2006.01)
  *C07K 14/24* (2006.01)
  *C12N 15/52* (2006.01)

(52) U.S. Cl.
  CPC ..... *C12P 7/6409* (2013.01); *C12Y 301/02014* (2013.01); *Y02P 20/52* (2015.11)

(56) References Cited

U.S. PATENT DOCUMENTS

| | | |
|---|---|---|
| 7,759,094 B2 | 7/2010 | Rieping |
| 7,901,924 B2 | 3/2011 | San |
| 8,709,753 B2 | 4/2014 | San |
| 2005/0196866 A1 | 9/2005 | San |
| 2006/0046288 A1 | 3/2006 | Ka-Yiu et al. |
| 2008/0038787 A1 | 2/2008 | Zelder |
| 2008/0160585 A1 | 7/2008 | Zelder |
| 2011/0124063 A1* | 5/2011 | Lynch ............ C10L 1/026 435/134 |
| 2011/0165637 A1 | 7/2011 | Pfleger et al. |
| 2011/0195505 A1 | 8/2011 | Euler |
| 2012/0237987 A1* | 9/2012 | Curtiss, III ............ C12N 1/20 435/134 |
| 2013/0203137 A1 | 8/2013 | San |

FOREIGN PATENT DOCUMENTS

| | | |
|---|---|---|
| WO | 2011059745 | 5/2011 |
| WO | WO2011059745 | 5/2011 |
| WO | 2011116279 | 12/2011 |

OTHER PUBLICATIONS

Fujita Y, et al., "Regulation of fatty acid metabolism in bacteria". Mol Microbiol. Nov. 2007;66(4):829-39.

Lu, X., et al. "Overproduction of free fatty acids in *E. coli*: Implications for biodiesel production". Metabolic Engineering. 2008, 10: 333-339.

Zhang X, et al. "Efficient free fatty acid production in *Escherichia coli* using plant acyl-ACP thioesterases Metabolic Engineering", Metab Eng., Nov. 2011; 13(6):713-22.

Sridhar Ranganathan et al: "An integrated computational and experimental study for overproducing fatty acids in *Escherichia coli*", Metabolic Engineering, vol. 14, No. 6, Oct. 2 2812 (2812-18-82), pp. 687-784.

Ranganathan, Sridhar et al. "An integrated computational and experimental study for overproducing fatty acids in *Escherichia coli*" Metabolic Engineering 14 (2012) 687-704.

Extended European Search Report for EP 12 84 2369, issued Jul. 3, 2015.

* cited by examiner

Fatty acid elongation cycle

Cell Viability of strain MLK163_18Z

US 9,598,696 B2

BACTERIA AND METHOD FOR SYNTHESIZING FATTY ACIDS

PRIOR RELATED APPLICATIONS

This application is a National Phase filing under 35 U.S.C. §371 of International Application PCT/US2012/060471 filed on Oct. 16, 2012 which claims priority to U.S. Provisional Applications 61/548,005, filed Oct. 17, 2011, and 61/548,399, filed Oct. 18, 2011. Each of these applications is incorporated by reference in its entirety for all purposes.

FEDERALLY SPONSORED RESEARCH STATEMENT

This invention was made with government support under Grant No: EEC-0813570 awarded by the National Science Foundation. The government has certain right in the invention.

FIELD OF THE INVENTION

The invention relates to a method of increasing the production of fatty acids by using genetically engineered microorganisms.

BACKGROUND OF THE INVENTION

Increasing energy costs and environmental concerns have emphasized the need to produce sustainable renewable fuels and chemicals. Fatty acids are composed of long alkyl chains and represent nature's "petroleum," being a primary metabolite used by cells for both chemical and energy storage functions. These energy-rich molecules are today isolated from plant and animal oils for a diverse set of products ranging from fuels to oleochemicals.

Whereas microbial fermentation processes for producing ethanol and related alcohol biofuels are well established, biodiesel (methylesters of fatty acids) is the major long chain product produced biologically, and it is almost exclusively derived from plant oils today. However, slow cycle times for engineering oil seed metabolism and the excessive accumulation of glycerol as a byproduct are two major drawbacks of deriving biodiesel from plants. Although most bacteria do produce fatty acids as cell envelope precursors, the biosynthesis of fatty acids is tightly regulated at multiple levels and large quantities are not made. Thus, the production of fatty acids from bacteria has not yet reached the point where it is cost effective.

The ability to produce free fatty acid at high yields and high rates by the metabolically engineered strains would provide an efficient framework to produce a large class of other derived products (chemicals and biofuels) either biologically or chemically. For example, as shown in FIG. 1, by introducing additional appropriate pathways, fatty acids can be converted to chemicals such as hydrocarbons, fatty alcohols, hydroxyl fatty acids, dicarboxylic acids etc. Likewise, the omega-end of the molecules can be modified by changing the starting precursors in the initial step of the fatty acid biosynthesis pathway (marked by white block arrows). Furthermore, the chain length of these molecules can be changed by using appropriate acyl-ACP thioesterases specific to a particular chain length, such as C8, C10, C12 or C14. In addition, various molecules can also be tapped out at different points during the fatty acid elongation cycle.

U.S. Pat. No. 7,759,094 discloses a method for the production of L-amino acids by fermentation of genetically engineered microorganisms, in which fadR is overexpressed and sucC is also overexpressed. However, there is no teaching with regard to the production of fatty acid in this patent.

U.S. Pat. No. 7,553,645 discloses a process for preparing L-amino acids using a genetically engineered or transformed microorganism, in which sucC is overexpressed. However, there is no teaching with regard to the production of fatty acid in this patent.

U.S. Pat. No. 7,211,415 also discloses a process for producing L-amino acids by fermentation of genetically engineered microorganisms of the Enterobacteriaceae family, in which sucC is overexpressed. However, there is no teaching with regard to the production of fatty acid in this patent.

US20110195505 discloses a genetically engineered lactobacillus for butanol production, in which deletion at fabZ1 results in 10% increase in total cell membrane saturated fatty acids. However, there is no teaching regarding the effect of fabZ overexpression on the production of fatty acids.

US20080160585 and US20080038787 disclose a method of increasing the production of lysine from a microorganism, in which sucC is deregulated. However, no detail was disclosed as to what extent of deregulation is involved, such as overexpressed, reduced or inactivated, nor on how to achieve the deregulation.

US20060046288 discloses a mutant *E. coli* strain with increased succinic acid production, in which it has reduced activity of fadR gene. However, no detail regarding the fadR gene or the regulation/mutation thereof is specifically disclosed.

WO2011116279 discloses hybrid ACP thioesterases, which can be combined with deletions in native fadD, and sucC. They also teach acidifying the medium to increase production of fatty acids.

Therefore, there is a need in the art for a biological system of producing fatty acids that is more efficient and cost effective than heretofore realized.

SUMMARY OF THE INVENTION

The invention relates to the production of fatty acid by genetically engineered microorganisms, in particular to engineered microorganisms that produce large amounts of free fatty acids by virtue of the addition of, for example, a plant acyl-ACP thioesterase and manipulation of the transcription factor(s) involved in the fatty acid biosynthesis and/or degradation pathways; a combination of these transcription factor(s) together with one or more of selected gene(s) in the fatty acid synthesis pathway, fatty acid degradation pathway or the central metabolic pathway.

This invention will allow the production of free fatty acid with yield close to the maximum theoretical yield. As such, this invention will provide the necessary framework to produce many other products sharing or branching out from the fatty acid synthesis pathway economically. These products include hydrocarbons, fatty alcohols, hydroxy fatty acids, dicarboxylic acids etc.

In more detail, the invention is one or more of the following:

A genetically engineered bacteria for producing fatty acids, said bacteria comprising a genotype comprising:
  i) an overexpressed acyl ACP thioesterase (TE$^+$);
  ii) one or more of overexpressed FabZ$^+$, FadR$^+$, or FabH$^+$;
  iii) zero, one or more of ΔfadR, ΔsucC, ΔfabR, ΔfadD, ΔptsG;

with the proviso that said bacteria does not have a genotype of ΔfadD ΔsucC TE+.

A genetically engineered bacteria for producing fatty acids, said bacteria comprising a genotype comprising:
  i) an overexpressed acyl ACP thioesterase (TE+);
  ii) one or more of overexpressed FabZ+, FadR+, or FabH+;
  iii) zero, one or more of ΔfadR, ΔsucC, ΔfabR, ΔfadD, ΔptsG;
with the proviso that said bacteria is not fabA+ and does not have a genotype of ΔfadD ΔsucC TE+.

A genetically engineered bacteria of genotype comprising i) ΔsucC FabZ+TE−; ii) ΔsucC ΔfabR FabZ+TE−; iii) FabZ+ TE+; iv) ΔfabR FadR+TE+; or v) ΔsucC ΔfabR FadR+TE+; or ΔsucC FabZ−TE+; or ΔfadD ΔsucC FabZ+TE+.

A genetically engineered bacteria comprising a genotype selected from the group consisting of:
1) ΔfadD ΔfabR acyl-ACP thioesterase+
2) ΔfadD ΔfabR fabZ+ acyl-ACP thioesterase+
3) ΔfadD ΔfadR acyl-ACP thioesterase+
4) ΔfadD ΔfadR fabZ+ acyl-ACP thioesterase+
5) ΔfadD ΔfadR ΔfabR acyl-ACP thioesterase+
6) ΔfadD fabZ+ acyl-ACP thioesterase+
7) ΔfadD fadR+ acyl-ACP thioesterase+
8) ΔfadD ΔsucC ΔfabR acyl-ACP thioesterase+
9) ΔfadD ΔsucC ΔfabR fabZ+ acyl-ACP thioesterase+
10) ΔfadD ΔsucC ΔfadR acyl-ACP thioesterase+
11) ΔfadD ΔsucC ΔfadR fabZ+ acyl-ACP thioesterase+
12) ΔfadD ΔsucC ΔfabR ΔfadR acyl-ACP thioesterase+
13) ΔfadD ΔsucC fabZ+ acyl-ACP thioesterase+
14) ΔfadD ΔsucC fadR+ acyl-ACP thioesterase−
15) ΔfabR acyl-ACP thioesterase+
16) ΔfabR fabZ+ acyl-ACP thioesterase+
17) ΔfadR acyl-ACP thioesterase+
18) ΔfadR fabZ+ acyl-ACP thioesterase+
19) ΔfadR ΔfabR acyl-ACP thioesterase+
20) fabZ+ acyl-ACP thioesterase+
21) fadR+ acyl-ACP thioesterase+
22) ΔsucC ΔfabR acyl-ACP thioesterase+
23) ΔsucC ΔfabR fabZ+ acyl-ACP thioesterase+
24) ΔsucC ΔfadR acyl-ACP thioesterase+
25) ΔsucC ΔfadR fabZ+ acyl-ACP thioesterase+
26) ΔfadD ΔsucC ΔfabR ΔfadR acyl-ACP thioesterase+
27) ΔfadD ΔsucC fabZ+ acyl-ACP thioesterase+
28) ΔfadD ΔsucC fadR+ acyl-ACP thioesterase+
29) ΔfadD ΔfabR fadR+ acyl-ACP thioesterase+
30) ΔfabR fadR+ acyl-ACP thioesterase+
31) ΔfadD ΔsucC ΔfabR fadR+ acyl-ACP thioesterase+
32) ΔsucC ΔfabR fadR+ acyl-ACP thioesterase+
33) ΔfadD ΔptsG fabH+ acyl-ACP thioesterase+
34) ΔptsG fabH+ acyl-ACP thioesterase+

In another embodiment, every bacteria herein described with a null mutation (e.g., Δgene) can instead be Gene−. Thus, ΔfadD can be FadD−, ΔfadR can be fadR−, ΔfabR can be FabR−, ΔsucC can be SucC− and ΔptsG can be PtsG−, etc.

Any one of the herein described bacteria, which produce at least 14% more fatty acid than having a control microorganism having ΔfadD plus TE+. Preferably, said bacteria produces at least 45% more fatty acid, or at least 65% more fatty acid and most preferred, at least 80% more fatty acid than having a control microorganism having ΔfadD plus TE+.

A genetically engineered bacteria for producing increased amounts of fatty acids over a control bacteria lacking said genotype, said bacteria comprising a genotype selected from the group consisting of:
1. ΔsucC fabZ+ acyl-ACP thioesterase+
2. ΔsucC ΔfabR fabZ+ acyl-ACP thioesterase+
3. fabZ+ acyl-ACP thioesterase+
4. fadR+ acyl-ACP thioesterase+
5. ΔsucC ΔfabR acyl-ACP thioesterase+
6. ΔfabR acyl-ACP thioesterase+
7. ΔfadR fabZ+ acyl-ACP thioesterase+
8. ΔfabR fabZ+ acyl-ACP thioesterase+
9. ΔfadD ΔsucC fabZ+ acyl-ACP thioesterase+
10. ΔfadD ΔsucC ΔfabR fabZ+ acyl-ACP thioesterase+
11. ΔfadD fabZ+ acyl-ACP thioesterase+
12. ΔfadD fadR+ acyl-ACP thioesterase+
13. ΔfadD ΔsucC ΔfabR acyl-ACP thioesterase+
14. ΔfadD ΔfabR acyl-ACP thioesterase+
15. ΔfadD ΔfadR fabZ+ acyl-ACP thioesterase+
16. ΔfadD ΔfabR fabZ+ acyl-ACP thioesterase+
17. ΔfadD ΔfabR fadR+ acyl-ACP thioesterase+
18. ΔfabR fadR+ acyl-ACP thioesterase+
19. ΔfadD ΔsucC ΔfabR fadR+ acyl-ACP thioesterase+
20. ΔsucC ΔfabR fadR+ acyl-ACP thioesterase+

Other embodiments provide a genetically engineered Enterobacteriaceae or *Enterobacter* comprising ΔfadD ΔsucC FabZ+ TE+; or ΔfadD ΔsucC ΔfabR FabZ+ TE+; or ΔfadD FabZ+ TE+; or ΔsucC FabZ+ TE+ or ΔsucC ΔfabR FabZ+ TE+; or FabZ+ TE+, or any of the herein described bacteria. In yet other embodiments, the invention can easily be transferred to any bacteria with an equivalent gene set, e.g., in *Firmicutes, Actinobacteria, Spirochetes, Proteobacteria, Bacillus, Streptococcus, Lactobaccillus, Lactococcus, Citrobacter, Haemophilus, Actinomycetes, Cyanobacteria, Staphylococcus, Neisseria, Micrococcus, Aspergillus, Psuedomonas*, and the like. Since there are hundreds of completely sequenced bacterial genomes readily available (see en.wikipedia.org/wiki/List_of_sequenced_bacterial_genomes), a person of ordinary skill in the art can easily confirm homologous gene sets by comparison, esp. using protein sequences, which diverge less than gene sequences in the prokaryotes.

Methods of producing fatty acids are also provided, comprising culturing any genetically engineered bacteria as described herein in a culture medium under conditions effective for the production of fatty acids; and harvesting said fatty acids from said bacteria and/or the culture medium. Another embodiment comprises adding acetic acid to said culture medium and harvesting the fatty acids from said culture medium.

Another method of producing fatty acids is provided, comprising culturing a genetically engineered bacteria in a culture medium under conditions effective for the production of fatty acids; and harvesting said fatty acids from the microorganism and/or the culture medium, wherein the bacteria and the desired fatty acid profile are selected from the group consisting of those listed in Table 2. Alternatively, the bacteria and the fatty acid profile are selected from the group consisting of:

| Bacteria: | Fatty Acid Profile: |
|---|---|
| ΔfadD ΔfabR TE+ | about 60% C16:1 |
| ΔfadD ΔfadR TE+ | about 60% C14 |
| ΔfadD ΔfadR FabZ+ TE+ | about 60% C14 |
| ΔfadD FabA+ TE+ | about 90% C16 |

Acyl-acyl carrier protein (ACP) thioesterase (herein known as "TE") is an enzyme that terminates the intraplastidial fatty acid synthesis by hydrolyzing the acyl-ACP intermediates and releasing free fatty acids to be incorporated into glycerolipids. In plants, these enzymes are classified in two families, FatA and FatB, which differ in amino acid sequence and substrate specificity. Generally speaking, the N terminal (aa 1-98) of any acyl-ACP thioesterases controls the substrate specificity of the enzyme, and it is known how to change substrate specificity by swapping amino terminal domains.

Bacteria already have native acyl-ACP thioesterase proteins that can be used in the invention (e.g., FadM, TesA, TesB). These can be used as is, or up regulated or otherwise made to be overexpressed. However, any acyl-ACP thioesterase can also be added to the bacteria, and this is especially beneficial where one wants to generate a specific distribution of fatty acids, since the various enzymes have different substrate preferences, some producing longer fats and others short fats.

Many acyl-ACP thioesterase proteins are known and can be added to bacteria for use in the invention (e.g., CAA52070, YP_003274948, ACY23055, AAB71729, BAB33929, to name a few of the thousands of such proteins available), although we have used plasmids encoding plant genes herein. Such genes can be added by plasmid or other vector, or can be cloned directly into the genome. In certain species it may also be possible to genetically engineer the endogenous protein to be overexpressed by changing the regulatory sequences or removing repressors. However, overexpressing the gene by inclusion on selectable plasmids that exist in hundreds of copies in the cell may be preferred due to its simplicity, although permanent modifications to the genome may be preferred in the long term for genetic stability.

Other acyl ACP thioesterases include *Umbellularia californica* fatty acyl-ACP thioesterase (AAC49001), *Cinnamomum camphora* fatty acyl-ACP thioesterase (Q39473), *Umbellularia californica* fatty acyl-ACP thioesterase (Q41635), *Myristica fragrans* fatty acyl-ACP thioesterase (AAB71729), *Myristica fragrans* fatty acyl-ACP thioesterase (AAB71730), *Elaeis guineensis* fatty acyl-ACP thioesterase (ABD83939), *Elaeis guineensis* fatty acyl-ACP thioesterase (AAD42220), *Populus tomentosa* fatty acyl-ACP thioesterase (ABC47311), *Arabidopsis thaliana* fatty acyl-ACP thioesterase (NP_172327), *Arabidopsis thaliana* fatty acyl-ACP thioesterase (CAA85387), *Arabidopsis thaliana* fatty acyl-ACP thioesterase (CAA85388), *Gossypium hirsutum* fatty acyl-ACP thioesterase (Q9SQI3), *Cuphea lanceolata* fatty acyl-ACP thioesterase (CAA54060), *Cuphea hookeriana* fatty acyl-ACP thioesterase (AAC72882), *Cuphea calophylla* subsp. *mesostemon* fatty acyl-ACP thioesterase (ABB71581), *Cuphea lanceolata* fatty acyl-ACP thioesterase (CAC19933), *Elaeis guineensis* fatty acyl-ACP thioesterase (AAL15645), *Cuphea hookeriana* fatty acyl-ACP thioesterase (Q39513), *Gossypium hirsutum* fatty acyl-ACP thioesterase (AAD01982), *Vitis vinifera* fatty acyl-ACP thioesterase (CAN81819), *Garcinia mangostana* fatty acyl-ACP thioesterase (AAB51525), *Brassica juncea* fatty acyl-ACP thioesterase (ABI18986), *Madhuca longifolia* fatty acyl-ACP thioesterase (AAX51637), *Brassica napus* fatty acyl-ACP thioesterase (ABH11710), *Oryza sativa* (indica cultivar-group) fatty acyl-ACP thioesterase (EAY86877), *Oryza sativa* (japonica cultivar-group) fatty acyl-ACP thioesterase (NP_001068400), *Oryza sativa* (indica cultivar-group) fatty acyl-ACP thioesterase (EAY99617), and *Cuphea hookeriana* fatty acyl-ACP thioesterase (AAC49269).

In some embodiments, at least one acyl-ACP thioesterase gene is from a plant, for example overexpressed acyl-ACP thioesterase gene from *Ricinus communis* (XP_002515564.1), *Jatropha curcas* (ABU96744.1), *Diploknema butyracea* (AAX51636.1), *Cuphea palustris* (AAC49180.1), or *Gossypium hirsutum* (AAF02215.1 or AF076535.1), or an overexpressed hybrid acyl-ACP thioesterase comprising different thioesterase domains operably fused together (see WO2011116279, sequences expressly incorporated by reference herein). Preferably, the hybrid thioesterase includes an amino terminal region (~aa 1-98 controls substrate specificity) of the acyl-ACP thioesterase from *Ricinus communis* or a 70, 80, 90 or 95% homolog thereto, or any TE with the desired substrate specificity, operably coupled to the remaining portion of the thioesterase from another species. In such manner, enzyme specificity can be tailored for the use in question.

In particular, the microorganism can comprise an overexpressed hybrid acyl-ACP thioesterase comprising the amino terminal region of the thioesterase from *Ricinus communis* operably coupled to the carboxyl region of the thioesterase from another species. Such microorganisms can be combined with each of the other knock-out and overexpressions described herein.

As used herein, "enhanced amount" means>29% improvement in yield of fatty acids comparing to yield of fatty acids of the mutant strain ML103_18, which has inactivated fadD and overexpressed acyl-ACP thioesterase. Here the calculation of yield is determined by the ratio of grams of fatty acids produced to grams of glucose used. Preferably, >30, 35, 40, 45, 50, 60, 70 or 80% improvement is observed.

Although certain strains have a reduced total amount of fatty acids, they may still be valuable as producing a particular distribution of fats, and thus even such strains are claimed herein.

As used herein, "fatty acids" means any saturated or unsaturated aliphatic acids having the common formulae of $C_nH_{2n\pm x}COOH$, wherein x≤n, which contains a single carboxyl group.

As used herein, "reduced activity" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like.

By "knockout" or "null" mutant what is meant is that the mutation produces almost undetectable amounts of protein activity. A gene can be completely (100%) reduced by knockout or removal of part or all of the gene sequence. Use of a frame shift mutation, early stop codon, point mutations of critical residues, or deletions or insertions, and the like, can also completely inactivate (100%) gene product by completely preventing transcription and/or translation of active protein. All knockout mutants herein are signified by Δgene where the gene name is identified above in Table A.

As used herein, "overexpression" or "overexpressed" is defined herein to be at least 150% increase of protein activity as compared with an appropriate control species. Preferably, the activity is increased 200-500%. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

As used herein, all accession numbers are to GenBank unless indicated otherwise.

Exemplary gene or protein species are provided herein. However, gene and enzyme nomenclature varies widely, thus any protein (or gene encoding same) that catalyzes the same reaction can be substituted for a named protein herein. Further, while exemplary protein sequence accession numbers are provided herein, each is linked to the corresponding DNA sequence, and to related sequences. Further, related sequences can be identified easily by homology search and requisite activities confirmed as by enzyme assay, as is shown in the art.

E. coli gene and protein names (where they have been assigned) can be ascertained through ecoliwiki.net/ and enzymes can be searched through brenda-enzymes.info/. ecoliwiki.net/ in particular provides a list of alternate nomenclature for each enzyme/gene. Many similar databases are available including UNIPROTKB, PROSITE; 5 EC2PDB; ExplorEnz; PRIAM; KEGG Ligand; IUBMB Enzyme Nomenclature; IntEnz; MEDLINE; and MetaCyc, to name a few.

By convention, genes are written in italic, and corresponding proteins in regular font. E.g., fadD is the gene encoding FadD or acyl-CoA synthetase.

Generally speaking, we have used the gene name and protein names interchangeably herein, based on the protein name as provided in ecoliwiki.net. The use of a protein name as an overexpressed protein (e.g, FabH+) signifies that protein expression can occur in ways other than by adding a vector encoding same, since the protein can be upregulated in other ways. The use of FadD⁻ signifies that the protein can be downregulated in similar way, whereas the use of ΔfadD means that the gene has been directly downregulated.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

TABLE A

Abbreviations and Definitions

| gene name | Definition (Protein name) | Exemplary UNIPROTKB Acc. No. |
|---|---|---|
| fabA | Gene that encodes beta-hydroxydecanoyl thioester dehydrase (protein = FabA) | P0A6Q3 |
| fabB | Gene that encodes 3-oxoacyl-[acyl-carrier-protein] synthase (protein = FabB) | P0A953 |
| fabH | Gene that encodes 3-oxoacyl-[acyl-carrier-protein] synthase III (protein = FabH) | P0A6R0 |
| fabR | Gene that encodes DNA-binding transcription repressor (protein = FabR) | P0ACU5 |

TABLE A-continued

Abbreviations and Definitions

| gene name | Definition (Protein name) | Exemplary UNIPROTKB Acc. No. |
|---|---|---|
| fabZ | Gene that encodes a component of the complex 3R-hydroxymuristoyl acyl carrier protein (ACP) dehydratase (protein = FabZ) | P0A6Q6 |
| fadD | Gene that encodes acyl-CoA synthetase (protein = FadD) | P69451 |
| fadR | Gene that encodes DNA-binding transcriptional dual regulator of fatty acid metabolism (protein = FadR) | P0A8V6 |
| sucC | Gene that encodes succinyl-CoA synthetase, beta subunit (protein = SucC) | P0A836 |
| ptsG | Gene that encodes component of EIIGlc; enzyme II glc; Glucose phophotransferase enzyme IIBC(Glc); glucose permease (PtsG) | P69786 |
| TE | Any gene encoding an acyl ACP thioesterase (TE), not an assigned gene name, but used herein. | See throughout. |

DESCRIPTION OF EMBODIMENTS OF THE INVENTION

Figure 1:
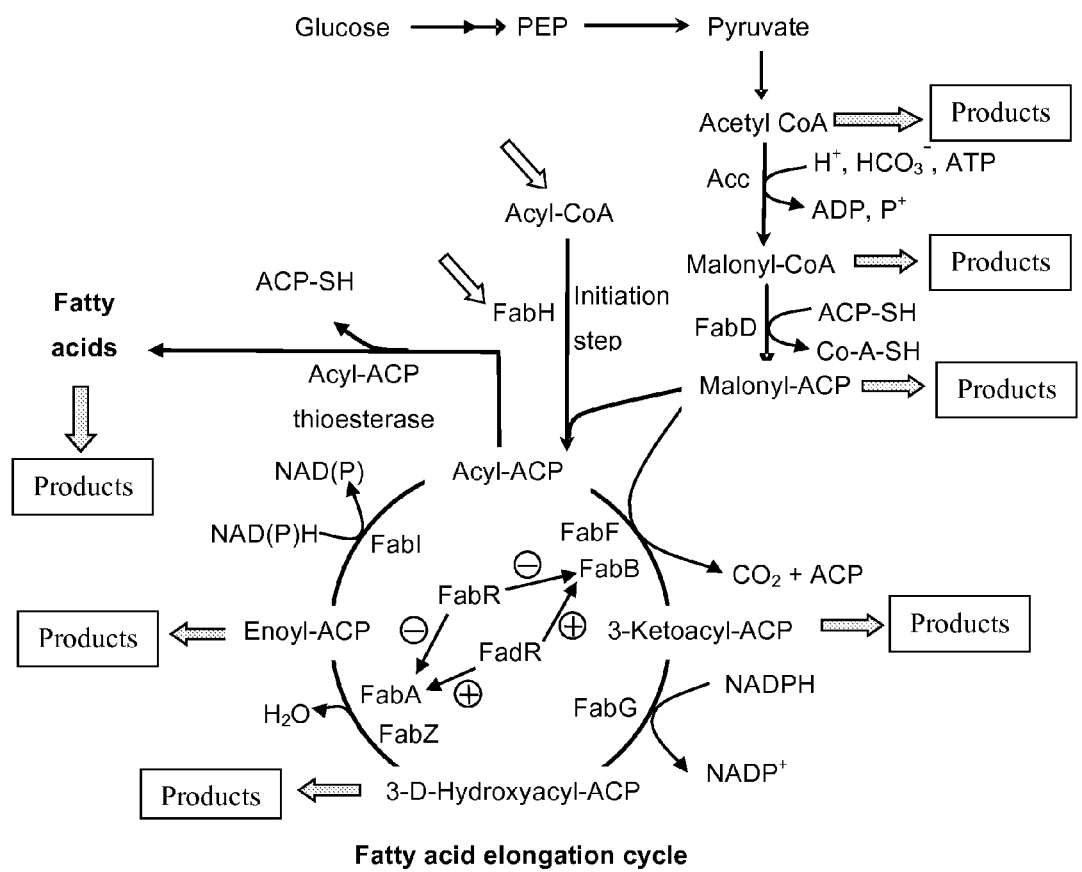
FIG. 1. Proposed metabolic map in which the introduction of additional appropriate pathways, the fatty acids can be converted to chemicals.
Figure 2:
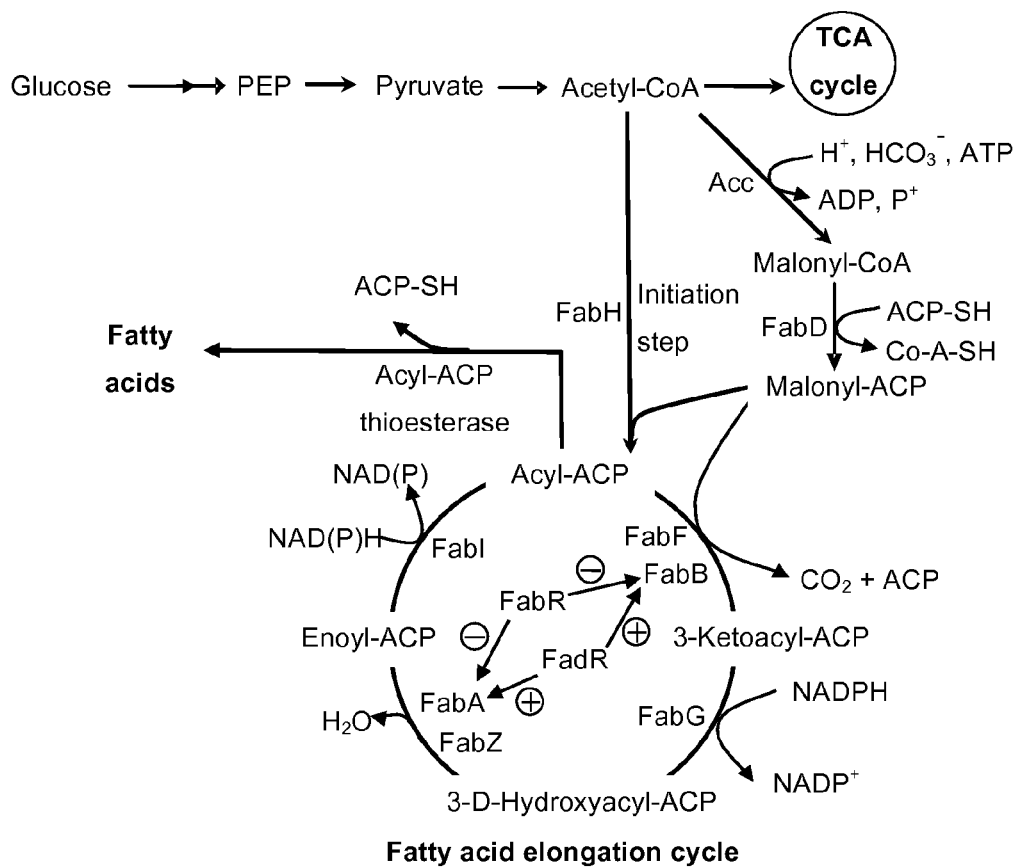
FIG. 2. Simplified metabolic map showing the fatty acid synthesis pathway. The transcription factor FabR has shown to have negative effect on FabA and FabB; but the transcription factor FadR has the opposite effect on FabA and FabB (Fujita et al., 2007). Free fatty acids are formed in the presence of an acyl-ACP thioesterase, which breaks the fatty acid elongation cycle.

FIG. 2 shows a simplified central aerobic metabolic pathway of *Escherichia coli* using glucose, for example, as a carbon source. Also included in FIG. 1 are the fatty acid biosynthesis pathways. Note that each fatty acid elongation cycle will increase the carbon chain length of the fatty acid by two. Free fatty acids can be produced by introducing an acyl-thioesterase gene. The presence of the thioesterase will break the fatty acid elongation cycle and release free fatty acids (Davis et al., 1993; Lu et al., 2008; Zhang et al., 2011).

Also shown in FIG. 1 are the two transcription factors involved in the fatty acid biosynthesis and degradation pathways. The transcription factor FabR has shown to have negative effect on FabA and FabB; but the transcription factor FadR has the opposite effect on FabA and FabB (Fujita et al., 2007).

Metabolically engineered strains were constructed based on the manipulation of the transcription factor(s) involved in the fatty acid biosynthesis and/or degradation pathways; a combination of these transcription factor(s) together with one or more of selected gene(s) in the fatty acid synthesis pathway, fatty acid degradation pathway or the central metabolic pathway.

Creating Strains

The wild type *E. coli* strain was MG 1655 (F⁻ lambda⁻ ilvG⁻ rfb⁻ rph⁻ ATCC 47076). An fadD knockout was introduced to make ML103 (MG1655 (ΔfadD) (Zhang 2011). The plasmid for overexpression was pTrc99a, a cloning vector from AMERSHAM PHARMACIA®, but any suitable vector could be used.

In this work, we used acyl ACP thioesterase from castor bean, added by plasmid per our prior work. See Zhang 2011 (pXZ18-pTrc99a carries an acyl-ACP thioesterase from *Ricinus communis* (castor bean) (XM002515518). However, any suitable enzyme can be used, and many are available in suitable expression plasmids already. Another vector, pXZ18R, is the same gene in the plasmid pXZ18 but with the addition of a fadR gene from *E. coli*.

The strains studied in the present invention are created based on a fadD knock-out mutant strain ML103_18, where the 18 is a particular clone number. We used the fadD mutant strain as a base strain because it is often used in the literature and easily available. However, deleting this gene is completely optional, and it is not considered a critical component of the genetic background.

The mutational set includes knockouts of one or more of FadR, SucC, FabR, FadD together with wild type or overexpressed acyl-ACP thioesterase together with overexpressed FabZ and FadR. The gene set should not include overexpressed FabA.

| Knockout mutations | Wild type or Overexpression | Overexpression | BUT Excluding |
|---|---|---|---|
| Zero, one or more of ΔfadR, ΔsucC, ΔfabR, ΔfadD, ΔptsG | TE$^+$ from any species | one or more of fabZ$^+$, fadR$^+$, or fabH$^+$ | Optionally FabA$^{+**}$ ΔfadD ΔsucC acyl-ACP thioesterase+ bacteria with no further mutations |

**FabA is known to have negative effect when used with the full complement of mutations, but may be beneficial with certain subsets, and this is being tested.

While our overexpression constructs were made by adding plasmid to a wild type background, this is not the only way to generate overexpression, and if desired the wild type gene can be completely replaced, other vectors could be used, and or the wild type gene could be upregulated. Further, while our gene sets included knockout mutations for simplicity and ease of interpreting results, knockout mutations can be replaced with reduced activity mutations.

Measuring Fatty Acid Production

The metabolically engineered strains were studied in shake flasks. The strains were grown in 250 ml flasks, with 40 ml Luria-Bertani (LB) broth medium supplemented with 15 g/L of glucose, 1 mM IPTG, and appropriate amount of ampicillin. The cultures were grown in a rotary shaker at 250 rpm.

Samples of the media were taken at 24 and 48 hrs after inoculation. The fatty acids were analyzed and quantified by GC/MS and GC/FID after extraction. Odd number saturated straight chain fatty acids, such as C13, C15 and/or C17, were used as the internal standard. The results shown in the table are the sum of all major free fatty acids in the sample. The data shown are means for triplicate experiments at 48 hrs.

ML163 from WO2011116279 is very similar to MLK163_18 (bold font in Table 1) and has the same genetic construction of ΔfadD, ΔsucC and acyl-ACP thioesterase$^+$, though the MLK variant has a kanamycin marker.

ML103_18 (bold font) was chosen as the base or control strain in this work, although a bacteria wild type for the gene set in question would also be a suitable control, and the improvement in fatty acids levels would be even higher. Some constructs do not give a yield higher than ML163_18 (underlined in Table 1), a strain taught in earlier work. However, such strains may have other desirable properties, such as different fatty acid distribution and/or percentage excreted to the medium. Thus, such strains are included herein even though they may produce less fatty acid than strain ML163_18. Further, such strains when compared against wild type bacteria probably have some level of improved production.

From the results shown below in Table 1, positive effects were observed in the strains shaded grey, and the best producers are indicated with an arrow.

TABLE 1

Free fatty acid and yield (g of fatty acids produced/g of glucose used)

| Strain name | Relevant genotype | Free FA (g/l) | % improvement* | Yield (g FA/g glucose) | % improvement* |
|---|---|---|---|---|---|
| ML103_18 | ΔfadD acyl-ACP thioesterase$^+$ | 3.12 | — | 0.21 | — |
| MLK163_18 | ΔfadD, ΔsucC acyl-ACP thioesterase$^+$ | 3.96 | 27 | 0.27 | 29 |
| MLK211_18 | ΔfadD ΔfabR acyl-ACP thioesterase$^+$ | 3.73 | 20 | 0.25 | 19 |
| MLK211_18A | ΔfadD ΔfabR fabA$^+$ acyl-ACP thioesterase$^+$ | 0.79 | −75 | 0.09 | −57 |
| MLK211_18Z | ΔfadD ΔfabR fabZ$^+$ acyl-ACP thioesterase$^+$ | 3.62 | 16 | 0.24 | 14 |
| MLK225_18 | ΔfadD ΔfadR acyl-ACP thioesterase$^+$ | 2.57 | −18 | 0.17 | −19 |
| MLK225_18Z | ΔfadD ΔfadR fabZ$^+$ acyl-ACP thioesterase$^+$ | 3.71 | 19 | 0.25 | 19 |
| MLK227_18 | ΔfadD ΔfadR ΔfabR acyl-ACP thioesterase$^+$ | 2.25 | −28 | 0.17 | −19 |

TABLE 1-continued

Free fatty acid and yield (g of fatty acids produced/g of glucose used)

| | | | | | |
|---|---|---|---|---|---|
| ML103_18A | ΔfadD fabA+ acyl-ACP thioesterase+ | 0.44 | -86 | 0.07 | -67 |
| ML103_18Z | ΔfadD fabZ+ acyl-ACP thioesterase+ | 4.61 | 48 | 0.31 | 48 |
| ML103_18fadR | ΔfadD fadR+ acyl-ACP thioesterase+ | 4.19 | 34 | 0.27 | 29 |
| MLK212_18 | ΔfadD ΔsucC ΔfabR acyl-ACP thioesterase+ | 3.83 | 23 | 0.26 | 24 |
| MLK212_18A | ΔfadD ΔsucC ΔfabR fabA+ acyl-ACP thioesterase+ | 1.58 | -49 | 0.10 | -52 |
| MLK212_18Z | ΔfadD ΔsucC ΔfabR fabZ+ acyl-ACP thioesterase+ | 5.15 | 65 | 0.34 | 62 |
| MLK213_18 | ΔfadD ΔsucC ΔfadR acyl-ACP thioesterase+ | 2.75 | -12 | 0.19 | -10 |
| MLK213_18Z | ΔfadD ΔsucC ΔfadR fabZ+ acyl-ACP thioesterase+ | 0.32 | -90 | 0.06 | -71 |
| MLK228_18 | ΔfadD ΔsucC ΔfabR ΔfadR acyl-ACP thioesterase+ | 3.24 | 4 | 0.21 | 0 |
| MLK163_18A | ΔfadD ΔsucC fabA+ acyl-ACP thioesterase+ | 2.03 | -35 | 0.17 | -19 |
| MLK163_18Z | ΔfadD ΔsucC fabZ+ acyl-ACP thioesterase+ | 5.65 | 81 | 0.38 | 81 |
| MLK163_18fadR | ΔfadD ΔsucC fadR+ acyl-ACP thioesterase+ | 1.49 | -52 | 0.22 | 5 | fabA+ = overexpression of FabA by plasmid, plus wild type gene present
fabZ+ = overexpression of FabZ by plasmid, plus wild type gene present;
fadR+ = overexpression of FadR by plasmid, plus wild type gene present
acyl-ACP thioesterase+ = overexpression of castor bean acyl ACP TE, plus wild type present.
*percentage improvement based on ML103_18

Inactivation of the transcription factor FabR improves fatty acid production and yield for both the parent strain and the sucC mutant strain (MLK211 vs ML103_18 and MLK212 vs MLK163_18).

Overexpression of FabZ improves fatty acid production and yield for both the parent strain and the sucC mutant strain (ML103_18Z vs ML103_18 and MLK163_18Z vs MLK163_18). In fact, a combination of sucC inactivation and FabZ overexpression yield the best strain with a very high titer of 5.65 and a yield of 0.38 g/g (which is 81% improvement over the base strain ML103_18). The yield of 0.38 g/g is very close to the maximum theoretical value (The maximum theoretical yields of C14 and C16 straight chain fatty acids are 0.3629 and 0.3561 g/g, respectively).

Overexpression of FadR improves fatty acid production and yield for the parent strain (ML103_18fadR vs ML103_18).

Order of improvements: ΔsucC fabZ+>ΔsucCΔfabR fabZ+>fabZ+>fadR+>ΔsucC>ΔsucCΔfabR>ΔfabR or ΔfadR fabZ+>ΔfabR fabZ+. By extracting only those with positive results in Table 1, we have the following Table 1.1, wherein the bolded strain MLK163-18 is similar to strain ML 163.

TABLE 1.1

Free fatty acid and yield of positive strains

| Strain name | Relevant genotype | Free FA (g/l) | % improvement* | Yield (g/g) | % improvement |
|---|---|---|---|---|---|
| MLK163_18Z | ΔfadD ΔsucC fabZ+ acyl-ACP thioesterase+ | 5.65 | 81 | 0.38 | 81 |
| MLK212_18Z | ΔfadD ΔsucC ΔfabR fabZ+ acyl-ACP thioesterase+ | 5.15 | 65 | 0.34 | 62 |
| ML103_18Z | ΔfadD fabZ+ acyl-ACP thioesterase+ | 4.61 | 48 | 0.31 | 48 |
| ML103_18fadR | ΔfadD fadR+ acyl-ACP thioesterase+ | 4.19 | 34 | 0.27 | 29 |
| MLK163_18 | ΔfadD ΔsucC acyl-ACP thioesterase+ | 3.96 | 27 | 0.27 | 29 |

TABLE 1.1-continued

Free fatty acid and yield of positive strains

| Strain name | Relevant genotype | Free FA (g/l) | % improvement* | Yield (g/g) | % improvement |
|---|---|---|---|---|---|
| MLK212_18 | ΔfadD ΔsucC ΔfabR acyl-ACP thioesterase+ | 3.83 | 23 | 0.26 | 24 |
| MLK211_18 | ΔfadD ΔfabR acyl-ACP thioesterase+ | 3.73 | 20 | 0.25 | 19 |
| MLK225_18Z | ΔfadD ΔfadR fabZ+ acyl-ACP thioesterase+ | 3.71 | 19 | 0.25 | 19 |
| MLK211_18Z | ΔfadD ΔfabR fabZ+ acyl-ACP thioesterase+ | 3.62 | 16 | 0.24 | 14 |

Additionally, some negative effects have been observed in the following strains:

Overexpression of FabA significantly decreases fatty acid production and yield for both the parent strain and the ΔsucC mutant strain (ML103_18A vs MLK103_18 and MLK163_18A vs ML163_18).

Simultaneous deactivation of FadR and FabR also decreases fatty acid production and yield for the (MLK227_18 vs MLK103_18).

Additional strains we have tested and gave very good results are MLK211(pXZ18R) and MLK212(pXZ18R)— which are ΔfadD ΔfabR FadR+ acyl-ACP thioesterase+ and ΔfadD ΔsucC ΔfabR FadR+ acyl-ACP thioesterase+. We are planning to test ΔfadD ΔfabR acyl-ACP thioesterase+ FadR+ FabZ+ and ΔfadD ΔsucC ΔfabR acyl-ACP thioesterase+ FadR+ FabZ+, which we expect to give even better results.

As a result, it is clear that random overexpression or deletion of transcription factors and/or with genes in the fatty acid synthesis and central metabolic pathway may not necessarily lead to positive results. Our data demonstrated that a selected single or selected combination of these manipulations is required to increase the yield and titer as shown in Table 2.

Our invention also indicates that the long belief of the carboxylation of acetyl-CoA to malonyl-CoA is the limiting step of fatty acid biosynthesis may not necessarily be the case since we have constructed strains that can achieve high yield (close to maximum theoretical yield), high titer and high production rate of free fatty acids.

Distribution of Fatty Acids

The genetic manipulations demonstrated herein also have significant effect on the distribution of the free fatty acids (Table 2). As such, this invention also will allow the manipulation or tailoring of the type of fatty acids to be produced. For example, while the engineered strain ML103_18A can produce more than 88% of C16, the other engineered strains MLK225_18 and MLK225_18Z can produce about 60% of C14, and MLK211_18 can produce about 60% of C16:1.

This indicates that the exact genetic combination has a significant effect on the fatty acid composition, even one uses the same acyl-ACP thioesterase.

TABLE 2

Fatty acid distribution (Percentage of total)

| Strain name | Relevant genotype | C14 | C16:1 | C16 | C18:1 |
|---|---|---|---|---|---|
| ML103_18 | ΔfadD acyl-ACP thioesterase+ | 47.27 | 38.33 | 12.96 | 1.45 |
| MLK163_18 | ΔfadD, ΔsucC acyl-ACP thioesterase+ | 37.30 | 31.74 | 28.06 | 2.91 |
| MLK211_18 | ΔfadD ΔfabR acyl-ACP thioesterase+ | 19.14 | 59.12 | 17.50 | 4.24 |
| MLK211_18A | ΔfadD ΔfabR fabA+ acyl-ACP thioesterase+ | 16.28 | 15.45 | 64.40 | 3.88 |
| MLK211_18Z | ΔfadD ΔfabR fabZ+ acyl-ACP thioesterase+ | 45.62 | 25.51 | 74.41 | 2.83 |
| MLK225_18 | ΔfadD ΔfadR acyl-ACP thioesterase+ | 59.63 | 23.36 | 14.02 | ND |
| MLK225_18Z | ΔfadD ΔfadR fabZ+ acyl-ACP thioesterase+ | 58.56 | 3.05 | 38.40 | ND |
| MLK227_18 | ΔfadD ΔfadR ΔfabR acyl-ACP thioesterase+ | 48.40 | 34.39 | 17.09 | 0.13 |
| ML103_18A | ΔfadD fabA+ acyl-ACP thioesterase+ | 10.92 | 0.00 | 89.08 | ND |
| ML103_18Z | ΔfadD fabZ+ acyl-ACP thioesterase+ | 57.91 | 8.16 | 33.92 | ND |
| ML103_18fadR | ΔfadD fadR+ acyl-ACP thioesterase+ | 18.29 | 48.09 | 26.85 | 6.77 |
| MLK212_18 | ΔfadD ΔsucC ΔfabR acyl-ACP thioesterase+ | 18.52 | 57.59 | 18.50 | 5.40 |
| MLK212_18A | ΔfadD ΔsucC ΔfabR fabA+ acyl-ACP thioesterase+ | 11.91 | 10.33 | 76.32 | 1.44 |
| MLK212_18Z | ΔfadD ΔsucC Δ fabR fabZ+ acyl-ACP thioesterase+ | 40.24 | 16.46 | 42.59 | 0.71 |
| MLK213_18 | ΔfadD ΔsucC ΔfadR acyl-ACP thioesterase+ | 55.95 | 27.05 | 16.31 | 0.69 |
| MLK213_18Z | ΔfadD ΔsucC ΔfadR fabZ+ acyl-ACP thioesterase+ | 44.58 | 3.51 | 43.74 | ND |
| MLK228_18 | ΔfadD ΔsucC ΔfabR ΔfadR acyl-ACP thioesterase+ | 38.26 | 38.13 | 22.78 | 0.83 |

TABLE 2-continued

| | | Fatty acid distribution (Percentage of total) | | | |
|---|---|---|---|---|---|
| Strain name | Relevant genotype | C14 | C16:1 | C16 | C18:1 |
| MLK163_18A | ΔfadD ΔsucC fabA+ acyl-ACP thioesterase+ | 20.95 | 7.50 | 71.55 | ND |
| MLK163_18Z | ΔfadD ΔsucC fabZ+ acyl-ACP thioesterase+ | 53.25 | 10.55 | 36.20 | ND |
| MLK163_18fadR | ΔfadD ΔsucC fadR+ acyl-ACP thioesterase+ | 14.24 | 38.39 | 35.78 | 11.59 |

ND: Not detected

Figure 3:
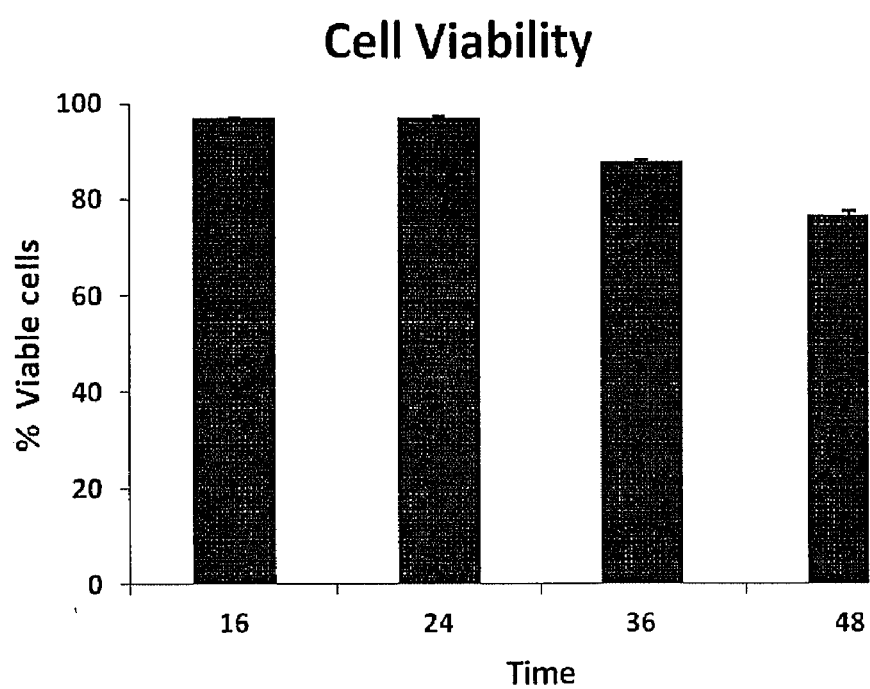
FIG. 3. Cell viability of strain MLK163_18Z, in which at least 75% of the cells are still viable after 48 hours growth.

The super-producer strain MLK163_18Z (ΔfadD ΔsucC fabZ+ acyl-ACP thioesterase−) was analyzed further by measuring the total cell dry weight. Samples were taken at 16, 24 36 and 48 hours after inoculation and tested for cell viability using propidium iodide staining of DNA and flow cytometry. The results are shown in FIG. 3.

Figure 4:
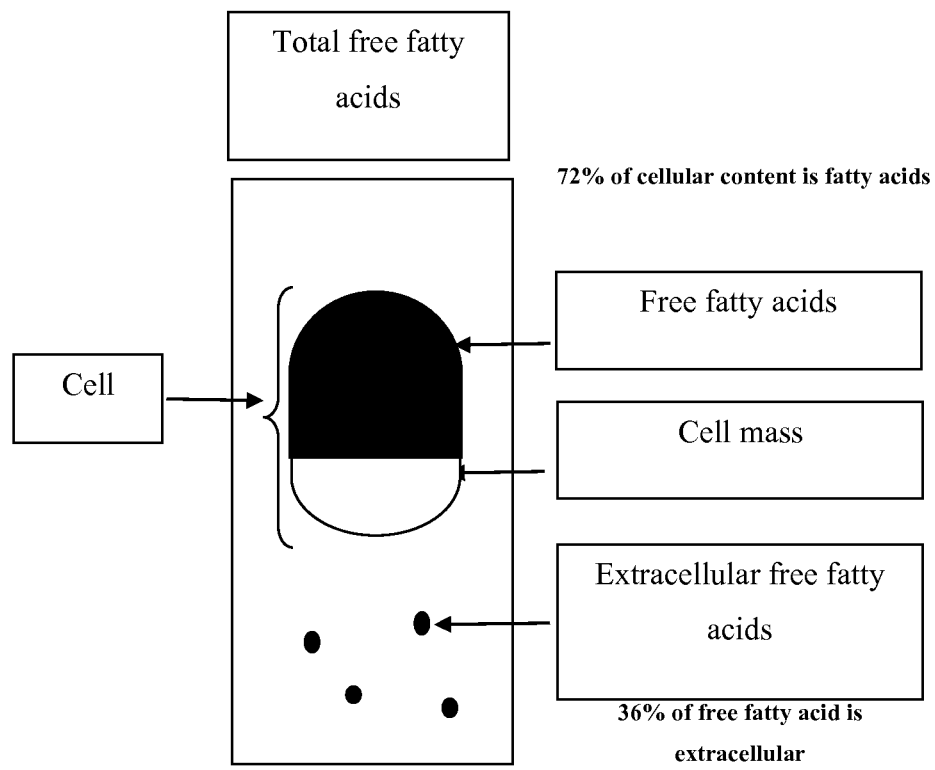
FIG. 4. Graphic illustrating that over 70% of the cellular content of the mutant strains are fatty acids.

It was found that at least more than 75% of the cells remained viable after 48 hrs. The dry weight of the sample at 48 hours was also determined and used to estimate the fraction of free fatty acid inside the cells. As explained in FIG. 4, certain amounts of free fatty acids are released from the cell, whereas a greater amount of free fatty acids are still located within the cells. It was found that free fatty acid accounts for more than 70% of the cellular contents.

FabH Overexpression

It has been reported that FabH is involved in the initiation of fatty acid biosynthesis, and we propose that overexpression of FabH may also contribute to the production of fatty acids. To study the impact of the initiation step in the fatty acids synthesis pathway, another engineered strain ML190_88-fabH (ΔfadD ΔptsG FabH+) carrying a modified acyl-ACP thioesterase from *C. palustris* (Acc. No. Q39554) specific to shorter chain length and with FabH from *E. coli* (UNIPROTKB Acc. No. P0A6R0) overexpression was constructed and tested in Super Broth (SB) medium with 30 g/L of glucose. The strain ML190_88 fabH s about 19% improvement in fatty acids production over the control strain ML190_88, as shown in Table 3.

TABLE 3

| | Free fatty acid (C8 straight chain fatty acid) | | |
|---|---|---|---|
| Strain name | Relevant genotype | Free FA (C8) (g/l) | % improvement* |
| ML190_88 | ΔfadD ΔptsG acyl-ACP thioesterase+ | 1.08 | — |
| ML190_88_fabH | ΔfadD ΔptsG fabH+ acyl-ACP thioesterase+ | 1.28 | 19 | fabH+ = overexpression of FabH by plasmid, plus wild type enzyme present

This result shows that with the same genetic background, overexpression of FabH improves fatty acid production. We will also plan to add FabH to the strains of Table 1.1, beginning with the best producers, such as ΔfadD ΔsucC FabZ+ TE+; ΔfadD ΔsucC ΔfabR FabZ− TE+; and ΔfadD FabZ+ TE+. Although not yet available, it is predicted that the combination with further improve fatty acid production levels, although the effect on distribution of fats is not yet known.

The present invention shows that manipulating repressor levels along with overexpression of certain fatty acid biosynthesis enzymes and overexpressed acyl ACP thioesterases can significantly increase fatty acid production, to level heretofore not thought possible. Further, the distribution of fatty acids can be manipulated by introducing different combinations of mutations. In addition, the present invention shows that overexpression of fabH can result in improvement of fatty acids production, at least in C-8 fatty acids.

The following publications are incorporated by reference in their entirety for all purposes herein.

Davies, H. M., et al., 1993. Fatty acid synthesis genes: Engineering the production of medium-chain fatty acids. p. 176-181. In: J. Janick and J. E. Simon (eds.), New crops. Wiley, N.Y.

Fujita Y, et al., Regulation of fatty acid metabolism in bacteria. Mol Microbiol. November 2007; 66(4):829-39.

Lu, X., et al., 2008. Overproduction of free fatty acids in *E. coli*: Implications for biodiesel production. Metabolic Engineering. 10: 333-339.

Zhang X, et al. 2011. Efficient free fatty acid production in *Escherichia coli* using plant acyl-ACP thioesterases Metabolic Engineering, Metab Eng. November 2011; 13(6): 713-22.

U.S. Pat. No. 7,759,094
U.S. Pat. No. 7,553,645
U.S. Pat. No. 7,211,415
US20110195505
US20080160585
US20080038787
US20060046288
WO2011116279

Campbell J W, Cronan J E Jr. 2001. *Escherichia coli* FadR positively regulates transcription of the fabB fatty acid biosynthetic gene. *J Bacteriol.* 183(20):5982-90.

What is claimed is:

1. A genetically engineered bacteria for producing fatty acids, said bacteria being Enterobacteriaceae and comprising a genotype comprising:
   a) an overexpressed acyl ACP thioesterase (TE+);
   b) one or more of an overexpressed FabZ+, FadR+, or FabH+;
   c) one or more of a ΔfadR, ΔsucC, ΔfabR, ΔfadD, or ΔptsG;
   with the proviso that said bacteria does not have a genotype of ΔfadD ΔsucC TE+,
   wherein said bacteria produces at least 14% more fatty acid than having a control microorganism having ΔfadD plus TE+.

2. The genetically engineered bacteria of claim 1, wherein the genotype of said bacteria comprises i) ΔsucC FabZ+ TE+; ii) ΔsucC ΔfabR FabZ+ TE+; iv) ΔfabR FadR+ TE+; or v) ΔsucC ΔfabR FadR+ TE+.

3. The genetically engineered bacteria of claim 1, wherein the genotype of said bacteria comprises ΔsucC FabZ+ TE+.

4. The genetically engineered bacteria of claim 1, wherein the genotype of said bacteria comprises ΔfadD ΔsucC FabZ+ TE+.

5. The genetically engineered bacteria of claim 1, wherein the genotype of said bacteria comprises a genotype selected from the group consisting of:
  (1) ΔfadD ΔfabR acyl-ACP thioesterase+
  (2) ΔfadD ΔfabR fabZ+ acyl-ACP thioesterase+
  (3) ΔfadD ΔfadR acyl-ACP thioesterase+
  (4) ΔfadD ΔfadR fabZ+ acyl-ACP thioesterase+
  (5) ΔfadD ΔfadR ΔfabR acyl-ACP thioesterase+
  (6) ΔfadD fabZ+ acyl-ACP thioesterase+
  (7) ΔfadD fadR+ acyl-ACP thioesterase+
  (8) ΔfadD ΔsucC ΔfabR acyl-ACP thioesterase+
  (9) ΔfadD ΔsucC ΔfabR fabZ+ acyl-ACP thioesterase+
  (10) ΔfadD ΔsucC ΔfadR acyl-ACP thioesterase+
  (11) ΔfadD ΔsucC ΔfadR fabZ+ acyl-ACP thioesterase+
  (12) ΔfadD ΔsucC ΔfabR ΔfadR acyl-ACP thioesterase+
  (13) ΔfadD ΔsucC fabZ+ acyl-ACP thioesterase+
  (14) ΔfadD ΔsucC fadR+ acyl-ACP thioesterase+
  (15) ΔfabR acyl-ACP thioesterase+
  (16) ΔfabR fabZ+ acyl-ACP thioesterase+
  (17) ΔfadR acyl-ACP thioesterase+
  (18) ΔfadR fabZ+ acyl-ACP thioesterase+
  (19) ΔfadR ΔfabR acyl-ACP thioesterase+
  (21) fadR+ acyl-ACP thioesterase+
  (22) ΔsucC ΔfabR acyl-ACP thioesterase+
  (23) ΔsucC ΔfabR fabZ+ acyl-ACP thioesterase+
  (24) ΔsucC ΔfadR acyl-ACP thioesterase+
  (25) ΔsucC ΔfadR fabZ+ acyl-ACP thioesterase+
  (26) ΔfadD ΔsucC ΔfabR ΔfadR acyl-ACP thioesterase+
  (27) ΔfadD ΔsucC fabZ+ acyl-ACP thioesterase+
  (28) ΔfadD ΔsucC fadR+ acyl-ACP thioesterase+
  (29) ΔfadD ΔfabR fadR+ acyl-ACP thioesterase+
  (30) ΔfabR fadR+ acyl-ACP thioesterase+
  (31) ΔfadD ΔsucC ΔfabR fadR+ acyl-ACP thioesterase+
  (32) ΔsucC ΔfabR fadR+ acyl-ACP thioesterase+
  (33) ΔfadD ΔptsG fabH+ acyl-ACP thioesterase+
  (34) ΔptsG fabH+ acyl-ACP thioesterase+.

6. The genetically engineered bacteria of claim 1, wherein said bacteria produces at least 45% more fatty acid than having a control microorganism having ΔfadD plus TE+.

7. The genetically engineered bacteria of claim 1, wherein said bacteria produces at least 65% more fatty acid than having a control microorganism having ΔfadD plus TE+.

8. The genetically engineered bacteria of claim 1, wherein said bacteria produces at least 80% more fatty acid than having a control microorganism having ΔfadD plus TE+.

9. A genetically engineered bacteria for producing increased amounts of fatty acids, said bacteria being Enterobacteriaceae and comprising a genotype selected from the group consisting of:
  (1) ΔsucC fabZ+ acyl-ACP thioesterase+
  (2) ΔsucC ΔfabR fabZ+ acyl-ACP thioesterase+
  (3) fadR+ acyl-ACP thioesterase+
  (4) fadR+ acyl-ACP thioesterase+
  (5) ΔsucC ΔfabR acyl-ACP thioesterase+
  (6) ΔfabR acyl-ACP thioesterase−
  (7) ΔfadR fabZ+ acyl-ACP thioesterase+
  (8) ΔfabR fabZ+ acyl-ACP thioesterase+
  (9) ΔfadD ΔsucC fabZ+ acyl-ACP thioesterase+
  (10) ΔfadD ΔsucC ΔfabR fabZ+ acyl-ACP thioesterase+
  (11) ΔfadD fabZ+ acyl-ACP thioesterase+
  (12) ΔfadD fadR+ acyl-ACP thioesterase+
  (13) ΔfadD ΔsucC ΔfabR acyl-ACP thioesterase+
  (14) ΔfadD ΔfabR acyl-ACP thioesterase+
  (15) ΔfadD ΔfadR fabZ+ acyl-ACP thioesterase+
  (16) ΔfadD ΔfabR fabZ+ acyl-ACP thioesterase+
  (17) ΔfadD ΔfabR fadR+ acyl-ACP thioesterase+
  (18) ΔfabR fadR+ acyl-ACP thioesterase+
  (19) ΔfadD ΔsucC ΔfabR fadR+ acyl-ACP thioesterase+
  (20) ΔsucC ΔfabR fadR+ acyl-ACP thioesterase+
  (21) ΔfadD ΔptsG fabH+ acyl-ACP thioesterase+.

10. A genetically engineered Enterobacteriaceae comprising ΔfadD ΔsucC FabZ+ TE+.

11. A genetically engineered Enterobacteriaceae comprising ΔfadD ΔsucC ΔfabR FabZ+ TE+.

12. A genetically engineered Enterobacteriaceae comprising ΔfadD FabZ+ TE+.

13. A genetically engineered Enterobacteriaceae comprising ΔsucC FabZ+ TE+.

14. A genetically engineered Enterobacteriaceae comprising ΔsucC ΔfabR FabZ+ TE+.

15. A method of producing fatty acids, comprising culturing a genetically engineered bacteria of any of claim 1-14 in a culture medium under conditions effective for the production of fatty acids; and harvesting said fatty acids from said bacteria and/or the culture medium.

16. The method of producing fatty acids of claim 15, comprising adding acetic acid to said culture medium and harvesting the fatty acids from said culture medium.

17. A method of producing fatty acids, comprising culturing a genetically engineered bacteria in a culture medium under conditions effective for the production of fatty acids; and harvesting said fatty acids from the microorganism and/or the culture medium, wherein the bacteria and the fatty acid profile are selected from the group consisting of those listed in Table 2.

18. The method of claim 17, wherein the bacteria and the fatty acid profile are selected from the group consisting of:

| Bacteria: | Fatty Acid Profile: |
| --- | --- |
| ΔfadD ΔfabR TE+ | about 60% C16:1 |
| ΔfadD ΔfadR TE+ | about 60% C14 |
| ΔfadD ΔfadR FabZ+ TE+ | about 60% C14 |
| ΔfadD FabA+ TE+ | about 90% C16 |

* * * * *